United States Patent
Yamamoto et al.

(10) Patent No.: US 6,696,595 B2
(45) Date of Patent: Feb. 24, 2004

(54) PROCESS OF THE PREPARATION OF HIGH-PURITY ALKYLADAMANTYL ESTERS

(75) Inventors: Hiromasa Yamamoto, Tokuyama (JP); Masao Yamaguchi, Tokuyama (JP); Yoshihiro Hirota, Tokuyama (JP); Takashi Kobayakawa, Tokuyama (JP)

(73) Assignee: Tokuyama Corporation, Yamaguchi-ken (JP)

( * ) Notice: Subject to any disclaimer, the term of this patent is extended or adjusted under 35 U.S.C. 154(b) by 0 days.

(21) Appl. No.: 10/296,320

(22) PCT Filed: May 15, 2001

(86) PCT No.: PCT/JP01/04036

§ 371 (c)(1),
(2), (4) Date: Nov. 22, 2002

(87) PCT Pub. No.: WO01/90045

PCT Pub. Date: Nov. 29, 2001

(65) Prior Publication Data

US 2003/0120107 A1 Jun. 26, 2003

(30) Foreign Application Priority Data

May 22, 2000  (JP) ........................................ 2000-149635

(51) Int. Cl.⁷ .............................................. C07C 69/52
(52) U.S. Cl. ...................................................... 560/220
(58) Field of Search ........................................ 560/220

(56) References Cited

FOREIGN PATENT DOCUMENTS

| EP | 0976702 A1 | * | 2/2000 |
|----|------------|---|--------|
| EP | 976702 A1 | | 2/2000 |
| EP | 0 976 702 A1 | | 2/2000 |
| GB | 1220477 A | | 1/1971 |
| GB | 1 220 477 A | | 1/1971 |
| JP | 5-265212 A | | 10/1993 |
| JP | 9-52864 A | | 2/1997 |
| JP | 2000-319226 A | | 11/2000 |
| JP | 2001-97893 A | | 4/2001 |
| JP | 2001-97924 A | | 4/2001 |

OTHER PUBLICATIONS

R. M. Acheson: "Chemistry of Heterocyclic Compound, Third Revised Edition" (Published in 1980 by Kagaku Gijutsu Syuppansya), pp. viii–xvi.

"Chemical Commodity Product of 13599" (Published in 1999 by Kagaku Kougyo Nippou Sya) pp. 960–971.

Epoxy Resin Handbook, (Published in 1987 by Nikkan Kougyo Shinbun Sya).

"New Epoxy Resin", (Published in 1975 by Syokodo) (special epoxy resin).

* cited by examiner

Primary Examiner—Alan L. Rotman
Assistant Examiner—Hector M Reyes
(74) Attorney, Agent, or Firm—Birch, Stewart, Kolasch & Birch, LLP

(57) ABSTRACT

There is provided a method for obtaining an alkyladamantyl ester efficiently by distilling and purifying a crude alkyladamantyl ester containing impurities which decompose the alkyladamantyl ester without decomposing the alkyladamantyl ester.

The crude alkyladamantyl ester such as crude 2-methyl-2-adamantyl methacrylate is distilled in the presence of a heterocyclic compound and/or a basic compound such as 3-ethyl-3-hydroxymethyloxetane or diglycidyl bisphenol A.

9 Claims, No Drawings

PROCESS OF THE PREPARATION OF HIGH-PURITY ALKYLADAMANTYL ESTERS

This application is the national phase under 35 U.S.C. § 371 of PCT International Application No. PCT/JP01/04036 which has an International filing date of May 15, 2001, which designated the United States of America.

TECHNICAL FIELD

The present invention relates to a method for producing a high purity alkyladamantyl ester by distilling and purifying a crude alkyladamantyl ester containing impurities.

BACKGROUND ART

Heretofore, when a solution to be distilled which contains a target compound also contains materials which promote decomposition of the target compound despite the fact that the target compound is a compound which is easily decomposed under influence of heat, a catalyst or the like, the target compound is easily decomposed during distillation. Therefore, it is difficult to obtain the target compound at a high purity or a high yield by purification by distillation. In general, even if a very small amount of materials which exhibit a decomposition promoting action is contained, it is very difficult to identify and remove the materials to such an amount that does not adversely affect the target compound because they cause decomposition of the target compound at the time of heating. In such a case, a purification method other than distillation must be used so as to purify a easily decomposable target compound with good reproducibility and at a high purity.

Meanwhile, demand for products of higher purity has been increasing every year. In particular, a reduction in metal components of a product used in a semiconductor production process is strongly demanded. As a purification method which can remove such metal components efficiently, purification by distillation is suitable.

In recent years, it has been reported that polymers obtained from alkyladamantyl esters having polymerizable groups have high dry etching resistance in a semiconductor production process (refer to JP-A 5-265212), and a possibility of their use as resist materials for semiconductors has been receiving attention. When these alkyladamantyl esters are used as resist materials for semiconductors, high purity alkyladamantyl esters having reduced metal components are required.

It is known that the alkyladamantyl ester can be produced by reacting 2-alkyl-2-adamantanol or 2-alkylideneadamantane which is obtained via 2-adamantanone from adamantane as a starting material or 2-adamantanone with an organometallic reagent such as methyl magnesium bromide so as to obtain a metal alkoxide and reacting a carboxylic acid derivative such as a carboxylic acid ester, a carboxylic anhydride or a carboxylic acid halide or a carboxylic acid with the obtained metal alkoxide.

In general, the alkyladamantyl ester is easily decomposed when stimulated by acid, heat or the like. For example, it is known that the alkyladamantyl ester is decomposed into a carboxylic acid or the like when heated in the presence of a catalytic amount of acid. By use of such a characteristic, the alkyladamantyl ester is used as a raw material for a chemically amplified resist in a semiconductor production process. Therefore, to purify the alkyladamantyl ester by distillation, it is commonly practiced to wash the alkyladamantyl ester with an alkali solution such as a sodium hydroxide solution as a pretreatment so as to remove acid components.

However, when a crude alkyladamantyl ester which has been subjected to a conventional pretreatment such as washing with an alkali solution so as to remove acid components is distilled by a commonly used method, the alkyladamantyl ester is decomposed during distillation for some reason, thereby producing a decomposition product such as a carboxylic acid or 2-alkylideneadamantane. Thus, a high purity alkyladamantyl ester has not been able to be obtained at a good yield.

Further, it has been found that a crude alkyladamantyl ester or a distilled and purified alkyladamantyl ester is decomposed during storage for some reason, thereby causing such a problem as coloration. In addition, it has also been found that an alkyladamantyl ester having a polymerizable group has a problem that when the alkyladamantyl ester is decomposed during storage to have coloration, a molecular weight does not increase even if it is polymerized.

DISCLOSURE OF THE INVENTION

An object of the present invention is to provide a method for producing a high purity alkyladamantyl ester by applying an efficient purification method to a crude alkyladamantyl ester for which an efficient distillation and purification method has not been known.

The present inventor has made intensive studies so as to solve the above problems. As a result, he has found that a crude alkyladamantyl ester can be purified efficiently by distilling the alkyladamantyl ester in the presence of a heterocyclic compound and/or a basic compound and that the above compounds also have an effect of improving storage stability of the alkyladamantyl ester. The present inventor has completed the present invention by these findings.

That is, the present invention is a method for producing a high purity alkyladamantyl ester which comprises the steps of esterifying an adamantane compound having an —OH group, —OM group or =R group (wherein M is an alkali metal atom or MgX (wherein X represents a halogen atom), and R is a divalent aliphatic hydrocarbon group) and distilling a crude alkyladamantyl ester obtained to form a high purity alkyladamantyl ester, wherein the distillation is carried out in the presence of a heterocyclic compound and/or a basic compound.

BEST MODE FOR CARRYING OUT THE INVENTION

In the present invention, a crude alkyladamantyl ester to be distilled is obtained by esterification of an adamantane compound having an —OH group, —OM group or =R group (wherein M is an alkali metal atom or MgX (wherein X represents a halogen atom), and R is a divalent aliphatic hydrocarbon group). The crude alkyladamantyl ester obtained by such a process contains an impurity which can decompose the alkyladamantyl ester. Although the impurity has not heretofore been identified yet, the present inventors assume that it may be a compound which decomposes under distillation conditions and produces acid.

In the —OH group, —OM group or =R group (wherein M is an alkali metal atom or MgX (wherein X represents a halogen atom), and R is a divalent aliphatic hydrocarbon group) in the adamantane compound which is a raw material of the crude alkyladamantyl ester, the alkali metal atom represented by M is a potassium atom, a sodium atom or the like, and the halogen atom represented by X is a chlorine atom, a bromine atom, an iodine atom or the like. Further, the divalent aliphatic hydrocarbon group represented by R is exemplified by a divalent group having 1 to 4 carbon atoms such as a methylidene group, an ethylidene group, a propylidene group, an isopropylidene group and the like.

Illustrative examples of the adamantane compound having the —OH group, —OM group or =R group include 2-alkyl-2-adamantanol (wherein the alkyl group has 1 to 6 carbon atoms) having an —OH group, 2-alkylideneadamantane (wherein the alkylidene group has 1 to 4 carbon atoms) having an =R group, and a compound represented by the following formula (1)

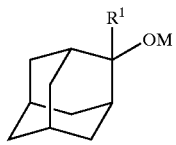

(1)

(wherein $R^1$ is a hydrogen atom or an alkyl group having 1 to 6 carbon atoms, and M is an alkali metal atom or MgX (wherein X represents a halogen atom)).

Illustrative examples of a specific production method of the crude alkyladamantyl ester include a method comprising the steps of alkylating 2-adamantanone with a Grignard reagent such as an alkyl magnesium halide or an organometallic reagent such as alkyl lithium so as to obtain an adamantane compound having an —OM group and then esterifying the adamantane compound with a carboxylic acid halide; a method comprising the steps of alkylating 2-adamantanone with an organometallic reagent so as to obtain 2-alkyl-2-admantanol and then esterifying the compound with a carboxylic acid halide, carboxylic anhydride or carboxylic acid ester; and a method comprising the steps of alkylating 2-adamantanone with an organometallic reagent, dehydrating an alcohol obtained from decomposition of a metal alkoxide so as to obtain 2-alkylideneadamantane and then esterifying the compound with a carboxylic acid by means of an addition reaction.

The crude alkyladamantyl ester may contain impurities other than the aforementioned impurity which decomposes the alkyladamantyl ester as long as the impurities are those which can be separated by distillation. Illustrative examples of such impurities include adamantane and 2-adamantanone which are used as a raw material upon synthesis of the alkyladamantyl ester, 1-adamantanol which is an impurity derived from the raw material, 1-adamatyl ester and 2-alkylideneadamantane which are by-produced at the time of the synthesis, and tetrahydrofuran and hexane which are used as a solvent at the time of the synthesis.

The content of these other impurities is not particularly limited. When the crude alkyladamantyl ester is produced by any of the above methods, a total amount of the other impurities is about 1 to 50 parts by weight when the weight of the alkyladamantyl ester is 100 parts by weight.

As the alkyladamantyl ester to be purified in the present invention, a compound represented by the following formula (2):

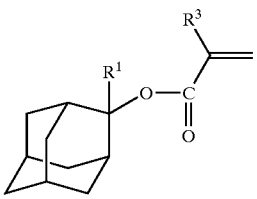

(2)

(wherein $R^2$ is a hydrogen atom or an alkyl group having 1 to 6 carbon atoms, and $R^3$ is a hydrogen atom or a methyl group) is preferably used.

Illustrative examples of the alkyl group having 1 to 6 carbon atoms which is represented by $R^2$ in the above formula (2) include linear alkyl groups such as a methyl group, ethyl group, propyl group, butyl group and hexyl group; and branched alkyl groups such as an isopropyl group, tertiary butyl group and neopentyl group. In particular, an alkyladamantyl ester represented by the above formula (2) in which $R^2$ is a methyl group, ethyl group or butyl group and $R^3$ is a hydrogen atom or methyl group is suitable since it is useful as a raw material for a resist for a semiconductor and a high degree of purification in particular is important.

In the present invention, the above crude alkyladamantyl ester is distilled in the presence of a heterocyclic compound and/or a basic compound (hereinafter also referred to as "decomposition inhibiting materials").

In the present invention, as the heterocyclic compound which is one of the decomposition inhibiting materials, a compound having, in a molecule, at least one heterocyclic ring having at least one hetero atom selected from the group consisting of oxygen, nitrogen, sulfur, selenium and silicon and 2 to 6 carbon atoms as ring-member atoms is preferably used. The heterocyclic compound may have a plurality of hetero atoms in the same heterocyclic ring. Further, the heterocyclic compound may have a plurality of the same or different heterocyclic rings in a molecule independently, and may have heterocyclic rings as condensed rings of the heterocyclic rings or as condensed rings of the heterocyclic rings and aromatic hydrocarbon rings.

As the heterocyclic compound, a known heterocyclic compound may be used without limitation. For example, such a compound as one described in "Chemistry of Heterocyclic Compound, Third Revised Edition" (published in 1980 by Kagaku Gijutsu Syuppansya) can be used.

As the heterocyclic ring contained in the heterocyclic compound in the present invention, a saturated three-to-five-membered ring is preferred. Illustrative examples of such a heterocyclic ring include cyclic ethers such as oxirane, oxetane and oxolane; cyclic thioethers such as thiirane, thiethane and thiolane; cyclic amines or N-alkyl substitution products thereof such as aziridine, N-methylaziridine and azetidine; cyclic siloxanes; and oxazines.

Of these, as a decomposition inhibiting material which exhibits a great effect of inhibiting decomposition of the alkyladamantyl ester and with which a higher purity target compound can be obtained, a heterocyclic compound having a cyclic ether structure in a molecule can be used. Above all, when a heterocyclic compound containing an oxirane ring or oxetane ring is used, it generally provides an effective decomposition inhibiting effect even in a small amount.

As the heterocyclic compound containing the cyclic ether structure, known compounds can be used without particular limitations. As the heterocyclic compound having the oxirane ring, compounds such as those described in a section in the 14$^{th}$ category (thermosetting resin) of "Chemical Commodity Product of 13599" (published in 1999 by Kagaku Kougyo Nippou Sya), in a section of the second chapter (epoxy resin) of "Epoxy Resin Handbook" (published in 1987 by Nikkan Kougyo Shinbun Sya) and in a section of the third chapter (special epoxy resin) of "New Epoxy Resin" (published in 1975 by Syokodo) can be used.

Illustrative examples of such compounds include oxirane compounds substituted by an alkyl group or an aryl group such as propylene oxide, 6,7-epoxydodecane, styrene oxide and α,α'-epoxydibenzyl; glycidyl ether compounds (including monomers and oligomers formed from two or more molecules) having a plurality of glycidyl groups such as phenyl glycidyl ether, glycerol diglycidyl ether, diglycidyl bisphenol A, brominated diglycidyl bisphenol A, diglycidyl bisphenol C, tetraglycidyl benzophenone, diglycidyl bisphenol F, triglycidyl-p-aminophenol, diglycidyl cyclohexane 1,3-dicarboxylate and novolac-type epoxy; glycidyl ester compounds such as diglycidyl phthalate, diglycidyl tetrahydrophthalate, diglycidyl hexahydrophthalate, glycidyl dimer acid ester, diglycidyl hexahydrophthalate and diglycidyl-p-oxybenzoic acid; alicyclic epoxy compounds such as vinylcyclohexene dioxide and 7-oxabicyclo[4.1.0]hepta-3-ylmethyl-7-oxabicyclo[4.1.0]heptane-3-carboxylate; glycidyl amine compounds such as tetraglycidyl diaminodiphenylmethane, triglycidyl p-aminophenol and diglycidyl aniline; and heterocyclic epoxys having other heterocyclic structures together with an oxirane ring such as 1,3-diglycidyl hydantoin, glycidyl glycideoxyethyl hydantoin and triglycidyl isocyanurate.

Further, illustrative examples of the heterocyclic compound having the oxetane ring include 3-ethyl-3-hydroxymethyloxetane and 1,4-bis{[(3-ethyl-3-oxetanyl)methoxy]methyl}benzene.

The basic compound which is the other decomposition inhibiting material is a compound which has an aqueous phase having a pH of larger than 7 when mixed with water (when not easily dissolved in water, a water-insoluble organic solvent such as hexane is further added thereto and shaken). Illustrative examples of such a basic compound include an oxide or hydroxide of an alkali metal or alkaline earth metal such as sodium hydroxide, potassium hydroxide, barium hydroxide, sodium oxide, magnesium oxide and calcium oxide; an inorganic weak base comprising a weak acid and a strong base such as potassium hydrogencarbonate, magnesium carbonate and sodium acetate; aluminum hydroxide and alumina; organic hydroxides such as tetramethylammonium hydroxide and tetrabutylammonium hydroxide; aliphatic amines such as triethylamine, trioctylamine, ethanolamine, diethanolamine and triethanolamine; aromatic amines such as pyridine, dimethylaminopyridine, phenothiazine, dibutylphenothiazine, dioctylphenothiazine, N,N'-diphenyl-p-phenylenediamine and N,N'-dinaphthyl-p-phenylenediamine; inorganic complex compounds such as hydrotalcite, e.g., $Mg_6Al_2(OH)_{16}CO_3.4H_2O$ and zeolite, e.g., A-type zeolite; Lewis bases; and the like.

The above decomposition inhibiting materials are preferably those which do not react with the alkyladamantyl ester which is the target compound and do not decompose under distillation conditions. Further, to obtain a high purity alkyladamantyl ester, these decomposition inhibiting materials are preferably those which are not distilled out together with the target compound or can be easily separated from the target compound to be distilled out even if contained in the target compound.

In order not to be distilled out together with the target compound, the decomposition inhibiting materials preferably shows such a high boiling point that does not allow the decomposition inhibiting materials to be distilled out at the time of distillation, has neither a boiling point nor a sublimation point or shows such a low boiling point that does not allow the decomposition inhibiting materials to be distilled out together with the target compound. Particularly, to maintain the decomposition inhibiting effect until completion of the distillation of the target compound, the decomposition inhibiting materials are more preferably compounds which show such a high boiling point which does not allow the compounds to be distilled out at the time of the distillation or have neither a boiling point nor a sublimation point.

In a case where decomposition inhibiting materials which can be easily separated from the target compound are used, even when the target compound is distilled out and mixed with the decomposition inhibiting materials as the distillation proceeds, the target compound can be obtained at a high purity since the decomposition inhibiting materials can be removed easily. For example, if the target compound does not have compatibility with the decomposition inhibiting materials, the target compound can be obtained easily through liquid separation. Further, if water-soluble decomposition inhibiting materials are used when the target compound is insoluble in water, the target compound can be obtained easily by washing a distillate with water. Further, if water-insoluble decomposition inhibiting materials are used when the target compound is easily soluble in water, an acid solution or an alkali solution, the target compound can be obtained easily by dissolving a distillate in water, an acid solution or an alkali solution, removing the decomposition inhibiting materials by a liquid separating operation or the like, performing a neutralization operation as required, and removing water. In addition, when the target compound is insoluble in water and stable in acid or alkali, acid or alkali decomposition inhibiting materials can be used. In this case, the target compound can be obtained easily by washing a distillate with an alkali or acid solution.

The decomposition inhibiting materials are added in an amount sufficient to maintain the decomposition inhibiting effect and inhibit decomposition of the target compound. The amount of the decomposition inhibiting materials should be determined in consideration of an amount of decomposition promoting materials and is generally 0.0001 to 500 parts by weight, preferably 0.1 to 10 parts by weight, based on 100 parts by weight of the crude alkyladamantyl ester.

In the production method of the present invention, distillation of the crude alkyladamantyl ester is carried out in the presence of the decomposition inhibiting materials. A means for adding the decomposition inhibiting materials to the crude alkyladamantyl ester is not particularly limited. For example, the decomposition inhibiting materials may be mixed with the crude alkyladamantyl ester prior to initiation of the distillation or may be fed to a distiller directly or through a distillation column, distillation tube or reflux line after the initiation of the distillation. Further, as the decomposition inhibiting materials, a plurality of compounds can be used in combination.

In the production method of the present invention, a mode in which the distillation is carried out in the presence of the decomposition inhibiting materials is not particularly limited, and simple distillation or fractional distillation is used. In the case of the fractional distillation, as a fractionating column, a thin-film fractionating column such as a vigoureux-type fractional column, a concentric fractional column, a spinning band fractional column and a packed fractional column or a plate fractionating column such as a bubble-cap fractionating column and a porous plate-type fractionating column is suitably used. Particularly, when vacuum distillation is performed, a thin-film fractionating column which undergoes little pressure loss is suitably used. Further, a known distillation mode such as a Kugel roll or thin-film distillation can be used without any limitations.

In addition, distillation conditions including temperature, pressure and a reflux ratio are not particularly limited and may be determined as appropriate according to composition of the crude alkyladamantyl ester, types and amounts of the decomposition inhibiting materials, purity of the target compound to be obtained at the end, and the like. When the alkyladamantyl ester is the compound represented by the above formula (2), conditions including a temperature of 80 to 150° C. and a pressure of 0.01 to 100 mmHg are preferably used.

As effects of the decomposition inhibiting materials, in addition to the above decomposition inhibiting effect, an effect of facilitating handling of the compound to be purified by decreasing the viscosity of the compound to be purified or forming the compound to be purified into a solution or suspension through addition of the decomposition inhibiting materials can also be expected, for example, even when the target compound is solid at room temperature. In a case where such an effect is expected, a liquid decomposition inhibiting material having a boiling point which is close to that of the target compound is suitably added, as a second decomposition inhibiting material, to the compound to be purified.

Further, in the present invention, the decomposition inhibiting materials also have an effect of improving storage stability of the alkyladamantyl ester. From the viewpoint of such an effect, as the decomposition inhibiting materials, a compound having an oxirane ring as a heterocyclic ring and an aromatic amine are particularly preferred among the aforementioned decomposition inhibiting materials.

In this case, the decomposition inhibiting materials are added in such an amount that can inhibit decomposition of a stored alkyladamantyl ester. The amount should be determined in consideration of efficacy of decomposition inhibiting materials to be used, solubility of the decomposition inhibiting materials against the alkyladamantyl ester and use of the alkyladamantyl ester. The amount is preferably 0.0001 to 100 parts by weight, more preferably 0.001 to 10 parts by weight, based on 100 parts by weight of the alkyladamantyl ester.

When it is not desirable that the decomposition inhibiting materials remain upon use of the target compound, decomposition inhibiting materials which can be easily separated from the target compound are preferably used so as to be able to remove the decomposition inhibiting materials easily by carrying out appropriate treatment before use of the target compound. As a method of separating the decomposition inhibiting materials from the target compound, methods which are the same as those mentioned above can be used.

EXAMPLES

The present invention will be further described with reference to Examples and Comparative Examples hereinafter. However, the present invention shall not be limited by these Examples in any way.

Synthesis Example 1

30 g of 2-adamantanone was dissolved in tetrahydrofuran anhydride. Then, 200 ml of solution of methyl magnesium bromide dissolved in tetrahydrofuran in an amount of 1 mol/liter was added thereto at room temperature. After 3 hours, 5 g of pyridine was added, 26 g of methacrylic acid chloride was then added, and the resulting mixture was stirred at 50° C. for 3 hours. After the obtained reaction mixture was concentrated, hexane and a 1N ammonium chloride solution were added to the mixture, and the resulting mixture was shaken to separate an organic phase. Then, the organic phase was washed with a 5% sodium hydroxide solution and then with water, and it was confirmed that the pH of an aqueous phase became 8. The washed organic phase was concentrated so as to obtain crude 2-methyl-2-adamantyl methacrylate containing 90% by weight of 2-methyl-2-adamantyl methacrylate.

Synthesis Example 2

70 g of 2-ethyl-2-adamantanol was dissolved in toluene, 1 g of p-toluenesulfonic acid was added, and water was removed by distillation by use of a Dean and Stark dehydrator under heating so as to obtain 2-ethylideneadamantane. To 50 g of the obtained 2-ethylideneadamantane, 500 g of methacrylic acid and 0.1 ml of concentrated sulphuric acid were added, and the resulting mixture was heated at 80° C. for 5 hours. After hexane was added to the obtained reaction mixture, the mixture was washed with water, a 5% sodium hydroxide solution, and water in turn, and it was confirmed that the pH of an aqueous phase became 8. After the washed organic phase was concentrated, unreacted 2-ethylideneadamantane was partially removed by sublimation so as to obtain crude 2-ethyl-2-adamantyl methacrylate containing 80% by weight of 2-ethyl-2-adamantyl methacrylate.

Example 1

To 100 parts by weight of the crude 2-methyl-2-adamantyl methacrylate obtained in Synthesis Example 1, 0.05 parts by weight of 3-ethyl-3-hydroxymethyloxetane was added as a decomposition inhibiting material, and the resulting mixture was distilled under a reduced pressure.

The reduced-pressure distillation was carried out at a temperature of 120° C. and a degree of vacuum of 0.3 mmHg by use of a 5-cm vigoureux fractionating column and a whole-condensation-type reflux fractionating device while air was being introduced by means of a glass capillary. A first distillate was removed, and a main distillate started to be collected at a point where purity of the 2-methyl-2-adamantyl methacrylate exceeded 80%. From the collected main distillate, 2-methyl-2-adamantyl methacrylate with a purity of 95.3 wt % could be obtained.

Example 2

To 100 parts by weight of the crude 2-methyl-2-adamantyl methacrylate obtained in Synthesis Example 1, 0.03 parts by weight of diglycidyl-bisphenol-A-based epoxy compound (mixture comprising diglycidyl bisphenol A (86 wt %) and a dimer of diglycidyl bisphenol A (14 wt %)) was added as a decomposition inhibiting material, and the resulting mixture was distilled under a reduced pressure.

The reduced-pressure distillation was carried out at a temperature of 120° C. and a degree of vacuum of 0.3 mmHg by use of a 5-cm vigoureux fractionating column and a whole-condensation-type reflux fractionating device while pure oxygen was being introduced by means of a glass capillary. A first distillate was removed, and a main distillate started to be collected at a point where purity of the 2-methyl-2-adamantyl methacrylate exceeded 80%. From the collected main distillate, 2-methyl-2-adamantyl methacrylate with a purity of 95.7 wt % could be obtained.

Example 3

Distillation was carried out in accordance with Example 1 except that 1 part by weight of 2-hexadecylthiirane was used as a decomposition inhibiting material based on 100 parts by weight of the crude 2-methyl-2-adamantyl methacrylate in place of 0.05 parts by weight of 3-ethyl-3-hydroxymethyloxetane, in Example 1. A first distillate was removed, and a main distillate started to be collected at a point where purity of the 2-methyl-2-adamantyl methacrylate exceeded 80%. From the collected main distillate, 2-methyl-2-adamantyl methacrylate with a purity of 93.4 wt % could be obtained.

Examples 4 to 10

As shown in Table 1, to 100 parts by weight of the crude 2-methyl-2-adamantyl methacrylate (indicated as "crude methyl compound" in Table 1) obtained in Synthesis Example 1 or 100 parts by weight of the crude 2-ethyl-2-adamantyl methacrylate (indicated as "crude ethyl compound" in Table 1) obtained in Synthesis Example 2, decomposition inhibiting materials shown in Table 1 were added in predetermined amounts, and distillations were carried out under a reduced pressure.

The reduced-pressure distillations were carried out at a temperature of 90 to 140° C. and a degree of vacuum of 0.1 to 0.3 mmHg by use of a 5-cm vigoureux fractionating column and a whole-condensation-type reflux fractionating device while air was being introduced by means of a glass capillary. Purities of thus obtained main distillates are shown in Table 1. As shown in Table 1, by use of the decomposition inhibiting materials of the present invention, high purity alkyladamantyl ester can be obtained.

TABLE 1

| Ex. No. | Crude Alkyladamantyl Ester 100 Parts By Weight | Decomposition Inhibiting Material Type | Amount Added (pbw) | Purity of Target Compound from Main Distillate (wt %) |
|---|---|---|---|---|
| 4 | Crude Methyl Compound | N, N'-naphthyl-p-phenylenediamine | 10 | 95.1 |
| 5 | Crude Methyl Compound | $Mg_6Al_2(OH)_{16}CO_3 \cdot 4H_2O$ | 1 | 97.6 |
| 6 | Crude Methyl Compound | diglycidyl bisphenol F | 0.1 | 96.3 |
| 7 | Crude Methyl Compound | tetraglycidyl diaminodiphenylmethane | 0.001 | 95.8 |
| 8 | Crude Ethyl Compound | 7-oxabicyclo[4.1.0]hepta-3-ylmethyl-7-oxabicyclo[4.1.0]heptane-3-carboxylate | 0.01 | 97.2 |
| 9 | Crude Ethyl Compound | dioctylphenothiazine | 5 | 93.4 |
| 10 | Crude Ethyl Compound | 1,4-bis{[(3-ethyl-3-oxetanyl)methoxy]methyl}benzene | 0.03 | 96.6 |

Ex.: Example pbw: parts by weight
Note 1) crude methyl compound: crude 2-methyl-2-adamantyl methacrylate obtained in Synthesis Example 1
Note 2) crude ethyl compound: crude 2-ethyl-2-adamantyl methacrylate obtained in Synthesis Example 2

Comparative Example 1

The crude 2-methyl-2-adamantyl methacrylate obtained in Synthesis Example 1 was distilled under a reduced pressure as it was. A first distillate was removed, and a main distillate started to be collected at a point where purity of the 2-methyl-2-adamantyl methacrylate exceeded 80%. From the collected main distillate, purity of the purified 2-methyl-2-adamantyl methacrylate was merely 85.3 wt %.

Examples 11 to 20

As shown in Table 2, to 100 parts by weight of the 2-methyl-2-adamantyl methacrylate (indicated as "methyl compound A" in Table 2) purified in Example 1 or 100 parts by weight of the 2-methyl-2-adamantyl methacrylate (indicated as "methyl compound B" in Table 2) purified in Comparative Example 1, decomposition inhibiting materials were added so as to examine storage stabilities at 40° C.

As shown in Table 2, storage stability of alkyladamantyl ester is improved by use of the decomposition inhibiting materials in the present invention.

TABLE 2

| Ex. No. | Alkyladamantyl Ester 100 Parts By Weight | Decomposition Inhibiting Material Type | Amount Added (parts by weight) | Discoloration after 3 Months |
|---|---|---|---|---|
| 11 | Methyl Compound A | diglycidyl bisphenol A | 0.01 | Not Occurred |
| 12 | Methyl Compound A | diglycidyl bisphenol A | 100 | Not Occurred |
| 13 | Methyl Compound A | tetraglycidyl diaminodiphenylmethane | 0.0001 | Not Occurred |
| 14 | Methyl Compound A | styrene oxide | 0.1 | Not Occurred |
| 15 | Methyl Compound A | 3-ethyl-3-hydroxymethyl-oxetane | 0.001 | Not Occurred |
| 16 | Methyl Compound A | $Mg_6A_{12}(OH)_{16}CO_3 \cdot 4H_2O$ | 0.01 | Not Occurred |
| 17 | Methyl Compound A | tetramethyl-hydroxide ammonium | 5 | Not Occurred |
| 18 | Methyl Compound B | $Mg_6A_{12}(OH)_{16}CO_3 \cdot 4H_2O$ | 0.02 | Not Occurred |
| 19 | Methyl Compound B | diglycidyl bisphenol A | 0.0001 | Not Occurred |
| 20 | Methyl Compound B | phenothiazine | 0.0001 | Not Occurred |
| C.Ex.2 | Methyl Compound A | Not Added | — | Colored Brown |
| C.Ex.3 | Methyl Compound B | Not Added | — | Colored Brown |

Ex.: Example C.Ex.: Comparative Example
Note 1) methyl compound A: purified 2-methyl-2-adamantyl methacrylate obtained in Example 1
Note 2) methyl compound B: purified 2-methyl-2-adamantyl methacrylate obtained in Comparative Example 1

As described above, according to the present invention, a crude alkyladamantyl ester which contains impurities that decompose the alkyladamantyl ester and has been difficult to purify by distillation can be easily purified by distillation. By use of the production method of the present invention, a high purity alkyladamantyl ester which is expected to be used as a resist material for a semiconductor can be obtained easily. Further, the alkyladamantyl ester can be stored stably over a long time period.

What is claimed is:

1. A method for producing a high purity alkyladamantyl ester which comprises the steps of esterifying a carboxylic acid or a derivative thereof with an adamantane compound having an —OH group, —OM group or =R group, wherein M is an alkali metal atom or MgX, wherein X represents a halogen atom, and R is a divalent aliphatic hydrocarbon group, and distilling a crude alkyladamantyl ester obtained to form a high purity alkyladamantyl ester, wherein the distillation is carried out in the presence of a heterocyclic compound which has, in a molecule, at least one saturated three-to-five-membered heterocyclic ring having at least one hetero atom selected from the group consisting of oxygen, nitrogen, sulfur, selenium and silicon.

2. The method of claim 1, wherein the adamantane compound is 2-alkyl-2-adamantanol, wherein the alkyl group has 1 to 6 carbon atoms, 2-alkylideneadamantane, wherein the alkylidene group has 1 to 4 carbon atoms, or a compound represented by the following formula (1):

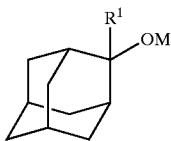
(1)

wherein $R^1$ is a hydrogen atom or an alkyl group having 1 to 6 carbon atoms, and M is an alkali metal atom or MgX, wherein X represents a halogen atom.

3. The method of claim 1, wherein the crude alkyladamantyl ester is obtained by esterifying 2-alkyl-2-adamantanol, wherein the alkyl group has 1 to 6 carbon atoms, 2-alkylideneadamantane, wherein the alkylidene group has 1 to 4 carbon atoms, or a compound represented by the following formula (1):

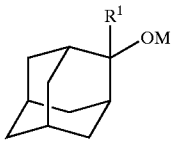
(1)

wherein $R^2$ is a hydrogen atom or an alkyl group having 1 to 6 carbon atoms, and M is an alkali metal atom or MgX, wherein X represents a halogen atom,
with a carboxylic acid, a carboxylic acid halide, a carboxylic anhydride or a carboxylic acid ester.

4. The method of claim 1, wherein the alkyladamantyl ester is a compound represented by the following formula (2):

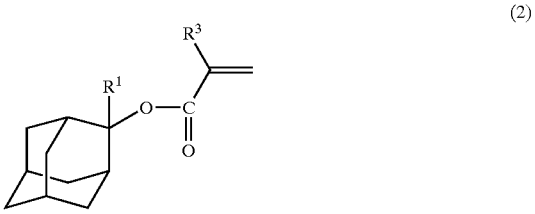
(2)

wherein $R^2$ is a hydrogen atom or an alkyl group having 1 to 6 carbon atoms, and $R^3$ is a hydrogen atom or a methyl group.

5. The method of claim 1, wherein the heterocyclic ring is oxirane, oxetane, oxolane, thiirane, thiethane, thiolane, aziridine, azetidine or an N-alkyl substituted compound thereof.

6. The method of claim 1, wherein the heterocyclic compound does not react with the alkyladamantyl ester and does not decompose under distillation conditions.

7. The method of claim 1, wherein the heterocyclic compound exhibits such a high boiling point that does not allow the compounds to be distilled out at the time of the distillation or has neither a boiling point nor a sublimation point.

8. The method of claim 1, which uses the heterocyclic compound in an amount of 0.0001 to 500 parts by weight based on 100 parts by weight of the crude alkyladamantyl ester.

9. An alkyladamantyl ester composition comprising 100 parts by weight of alkyladamantyl ester and 0.0001 to 100 parts by weight of heterocyclic compound which has, in a molecule, at least one saturated three-to-five-membered heterocyclic ring having at least one hetero atom selected from the group consisting of oxygen, nitrogen, sulfur, selenium and silicon.

* * * * *